United States Patent [19]

Guay et al.

[11] Patent Number: 5,968,958
[45] Date of Patent: Oct. 19, 1999

[54] 5-METHANESULFONAMIDO-3H-ISOBENZOFURAN-1-ONES AS INHIBITORS OF CYCLOOXYGENASE-2

[75] Inventors: Daniel Guay; Chun-Sing Li; Nathalie Ouimet, all of Kirkland, Canada

[73] Assignee: Merck Frosst Canada, Inc., Kirkland, Canada

[21] Appl. No.: 08/860,266

[22] PCT Filed: Jan. 29, 1996

[86] PCT No.: PCT/CA96/00062

§ 371 Date: Jun. 19, 1997

§ 102(e) Date: Jun. 19, 1997

[87] PCT Pub. No.: WO96/23786

PCT Pub. Date: Aug. 8, 1996

Related U.S. Application Data

[63] Continuation of application No. 08/381,164, Jan. 31, 1995, abandoned.

[51] Int. Cl.[6] .......................... A61K 31/44; C07D 405/02
[52] U.S. Cl. .......................... 514/337; 514/369; 514/376; 546/284.1; 548/228; 548/229; 548/225; 548/231; 548/187; 548/189
[58] Field of Search .................... 514/337, 369, 514/376; 546/284.1; 548/228, 229, 225, 231, 187, 189

[56] References Cited

U.S. PATENT DOCUMENTS

| | | | |
|---|---|---|---|
| 2,646,385 | 7/1953 | Lewenstein | 514/161 |
| 3,010,873 | 11/1961 | Cavallini et al. | 514/271 |
| 3,121,044 | 2/1964 | Buckwalter et al. | 424/472 |
| 3,128,226 | 4/1964 | Rubin et al. | 514/161 |
| 3,439,094 | 4/1969 | Emele | 514/264 |
| 3,840,597 | 10/1974 | Moore et al. | 564/97 |
| 4,244,960 | 1/1981 | Schroder et al. | 546/293 |
| 4,375,479 | 3/1983 | Schroeder et al. | 564/82 |
| 4,411,910 | 10/1983 | Schroeder et al. | 549/304 |
| 4,696,948 | 9/1987 | Petzoldt | 514/605 |
| 4,820,827 | 4/1989 | Haber | 549/78 |
| 4,866,091 | 9/1989 | Matsuo et al. | 558/413 |
| 4,885,367 | 12/1989 | Yoshikawa et al. | 546/216 |

FOREIGN PATENT DOCUMENTS

| | | |
|---|---|---|
| 0 009 554 | 4/1980 | European Pat. Off. . |
| 0 056 956 | 8/1982 | European Pat. Off. . |
| 0 140 684 | 5/1985 | European Pat. Off. . |
| 130870/86 | 1/1986 | Japan . |
| 242997/90 | 4/1992 | Japan . |
| WO 94/13635 | 6/1994 | WIPO . |
| WO 94/20480 | 9/1994 | WIPO . |

OTHER PUBLICATIONS

CA 124:86533 Li et al, 1995.
Rufer, et al., Chem. Abstracts, vol. 100, (1) Ab. #6113u, (1983).
K. Petzoldt, Chem. Abstracts, vol.104, Ab. #107904r (1985).
F. Berti, et al., Chem. Abstracts, vol. 113, Ab. #224303r (1990).
Boettcher, et al., Chem. Abstracts, vol. 107, Ab. #190553f (1987).
Boettcher, et al., Chem. Abstracts, vol. 110, (15) Ab. #128249v (1989).
D.P. Carr, et al., Chem. Abstracts, vol. 106, Ab. #60922u (1987).
C. Rufer, et al., Chem. Abstracts, vol. 98, Ab. #65117m (1982).
Gans, et al., Journal of Pharm. and Expirim. Ther., vol. 254 (1) pp. 180–187 (1990).
Hla, et al., Proc. Natl. Acad. Sci, vol. 89, pp. 7384–7388, Pharmacology, Aug. (1992).
Rufer, et al., Eur. J. Med. Chem. Chim. Ther., vol. 17, pp. 173–180 (1982).
D.P. Carr, et al., Agents and Actions, vol. 19, 5/6 (1986) pp. 374–375, "Comparison of the systemic inhibition of thromboxane synthesis, anti–inflammatory activity and gastro–intestinal toxicity . . . ".

*Primary Examiner*—Jane Fan
*Attorney, Agent, or Firm*—Richard C. Billups; Curtis C. Panzer; David L. Rose

[57] ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

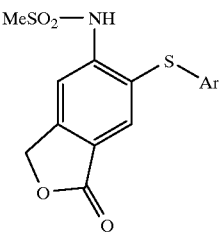

The invention also encompasses certain pharmaceutical compositions for treatment of cyclooxygenase-2 mediated diseases comprising compounds of Formula I.

12 Claims, No Drawings

5-METHANESULFONAMIDO-3H-ISOBENZOFURAN-1-ONES AS INHIBITORS OF CYCLOOXYGENASE-2

This is a 371 of PCT/CA96/00062 Jan. 29, 1996 now WO96/23786 which is continuation of Ser. No. 08/381,164 Jan. 31, 1995 abandoned.

BACKGROUND OF THE INVENTION

This invention relates to methods of treating cyclooxygenase mediated diseases and certain pharmaceutical compositions therefor.

Non-steroidal, anti-inflammatory drugs exert most of their anti-inflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar anti-inflammatory, antipyretic and analgesic properties to a conventional non-steroidal anti-inflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease and for decreasing bone loss particularly in postmenopausal women (i.e., treatment of osteoporosis).

A brief description of the potential utility of cyclooxygenase-2 is given in an article by John Vane, *Nature*, Vol. 367, pp. 215–216, 1994.

SUMMARY OF THE INVENTION

The invention encompasses compounds of Formula I as well as a method of treating cyclooxygenase-2 mediated diseases comprising administration to a patient in need of such treatment of a non-toxic therapeutically effective amount of a compound of Formula I.

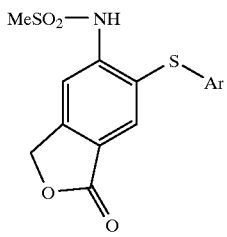

I

The invention also encompasses certain pharmaceutical compositions for treatment of cyclooxygenase-2 mediated diseases comprising compounds of Formula I.

DETAILED DESCRIPTION OF THE INVENTION

The invention encompasses a genus of compounds of Formula I

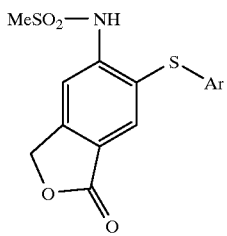

I and pharmaceutically acceptable salts thereof wherein
Ar is

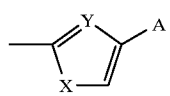

X is O or S,
Y is CH or N,
and A is selected from
 (a) hydrogen,
 (b) $C_{1-2}$ alkyl,
 (c) vinyl, and
 (d) acetylenyl;
or where Ar is

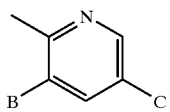

B and C are each independently
 (a) hydrogen,
 (b) F, Cl, Br or I,
 (c) methyl or ethyl,
 (d) vinyl or acetylenyl,
 (e) $OCH_3$ or $OCF_3$,
 (f) $SCH_3$, or $SCF_3$, (g) CN, or
(h) N$_3$.

Within this genus there is a class of compounds wherein
X is S,
Y is CH or N,
and A is selected from
(a) hydrogen,
(b) C$_{1-2}$ alkyl,
(c) vinyl, and
(d) acetylenyl;
B and C are each independently
(a) hydrogen,
(b) F, Cl, Br or I,
(c) methyl or ethyl,
(d) OCH$_3$ or OCF$_3$,
(e) SCH$_3$, or
(f) CN.

Whithin this class there is a subclass of compounds wherein
X is S,
Y is N,
and A is selected from
(a) hydrogen,
(b) C$_{1-2}$ alkyl,
(c) vinyl, and
B and C are each independently
(a) hydrogen,
(b) F, Cl or Br,
(c) methyl or ethyl,
(d) OCH$_3$,
(e) SCH$_3$, or
(f) CN.

Illustrating the invention are:
6-(4-Ethyl-2-thiazolythio)-5-methanesulfonamido-3H-isobenzofuran-1-one;
6-(5-Chloro-2-pyridylthio)-5-methanesulfonamido-3H-isobenzofuran-1-one;
6-(2-Thiazolythio)-5-methanesulfonamido-3H-isobenzofuran-1-one; and
5-Methanesulfonamido-6-(4-methyl-2-thiazolythio)-3H-isobenzofuran-1-one.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucarnine, glucosamine, histidine, hydrabarnine, isopropylarnine, lysine, methylglucamine, morpholine, piperazine, piperidine, polyamine resins, procaine, purines, theobromine, triethylarnine, trimethylamine, tripropylarnine, tromethamine, and the like.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, bums, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease and for decreasing bone loss particularly in postmenopausal women (i.e., treatment of osteoporosis).

By virtue of its high cyclooxygenase-2 (COX-2) activity and/or its specificity for cyclooxygenase-2 over cyclooxygenase-1 (COX-1), Compound I will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetomi-nophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example, peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods.

Method A

5-Chloro4-nitro-2-methylaniline II is converted to 5-chloro-4nitro-2-methylbenzonitrile III by Sandmeyer reaction. Bromination with N-bromosuccinimide yields 2-bromomethyl-5-chloro-4-nitrobenzonitrile. Upon hydrolysis in aqueous sulfuric acid or via the displacement with sodium acetate followed by hydrolysis gives 6-chloro-5-nitro-3H-isobenzofuran-1-one IV. Reduction with diisobutylaluminum hydride and acetalization provides 6-chloro-1-methoxy-5-nitro-1,3-dihydrobenzofuran V. Coupling with an arylthiol (ArSH) proceeds under basic conditions with or without the presence of a copper salt. Hydrolysis of the methoxy acetal followed by oxidation with a chromate salt affords the 5-nitro-3H-isobenzofuran-1-one VI. Reduction of the nitro group with iron powder or tin (II) chloride yields the corresponding amino intermediate. Treatment with excess methanesulfonyl chloride in the presence of triethylamine gives the bissulfonamide, which upon subsequent hydrolysis with sodium hydroxide furnishes the title Compound I.

METHOD A

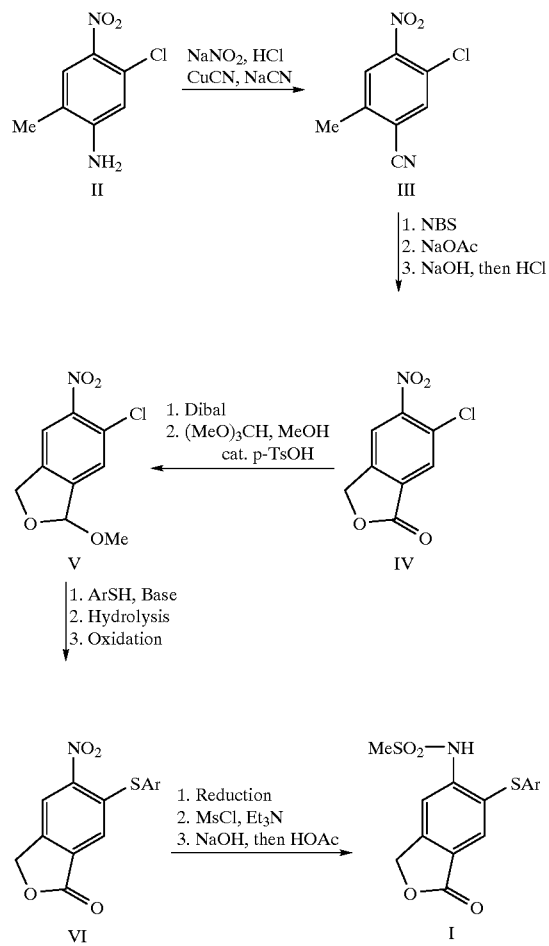

Method B

4Chloro-3-nitrobenzaldehyde VII is coupled with an arylthiol (ArSH) under basic conditions. Reduction of the aldehyde and protection of the resulting alcohol as an acetate yields Compound VIII. The nitro group is then reduced with iron powder or tin (II) chloride and reacted with methanesulfonyl chloride in the presence of pyridine to give sulfonamide IX. Nitration of sulfonamide IX occurs predominantly para to the sulfonamide group. Upon hydrogenation, followed by diazotization, treatment with sodium iodide and hydrolysis with sodium hydroxide provides aryl iodide X. A palladium catalyzed carbonylation reaction then affords the title Compound I.

METHOD B
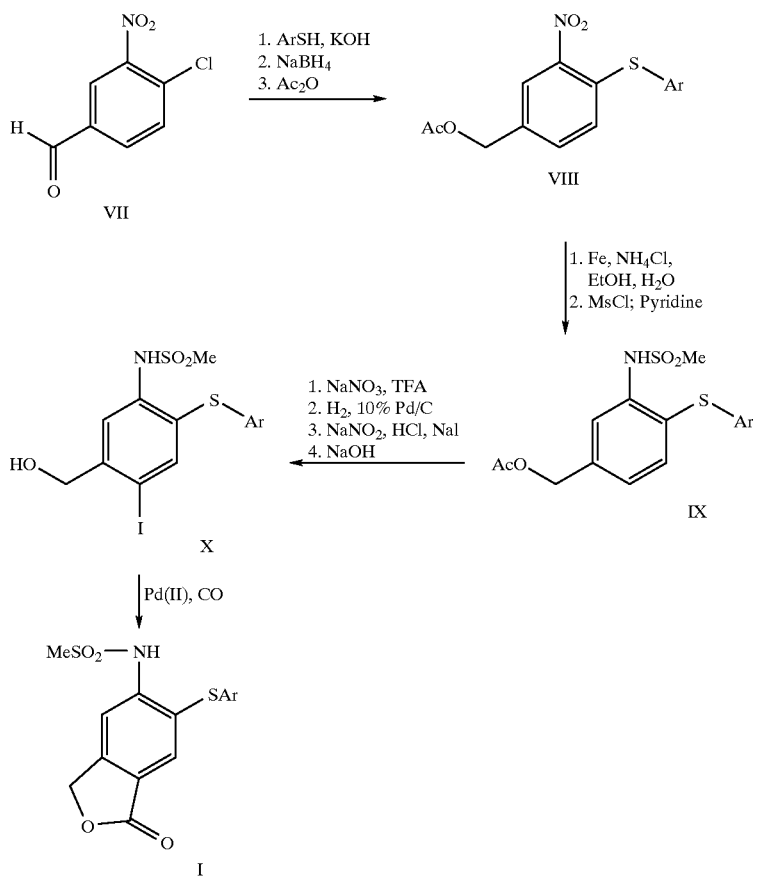
Table I illustrates compounds of Formula Ia, which are representative of the present invention.
TABLE 1
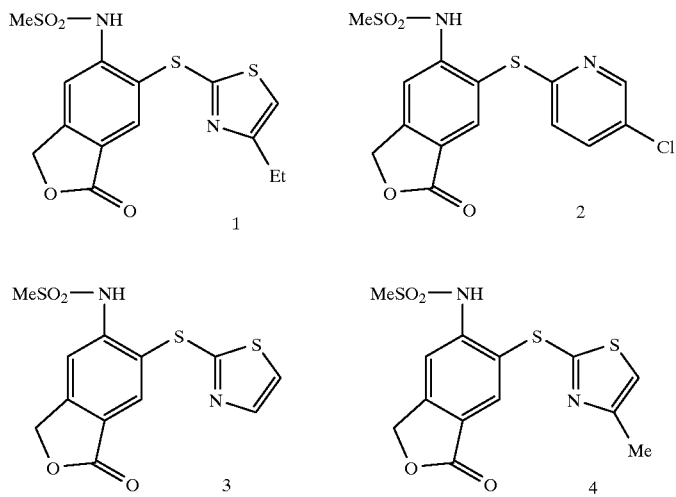

TABLE 1-continued

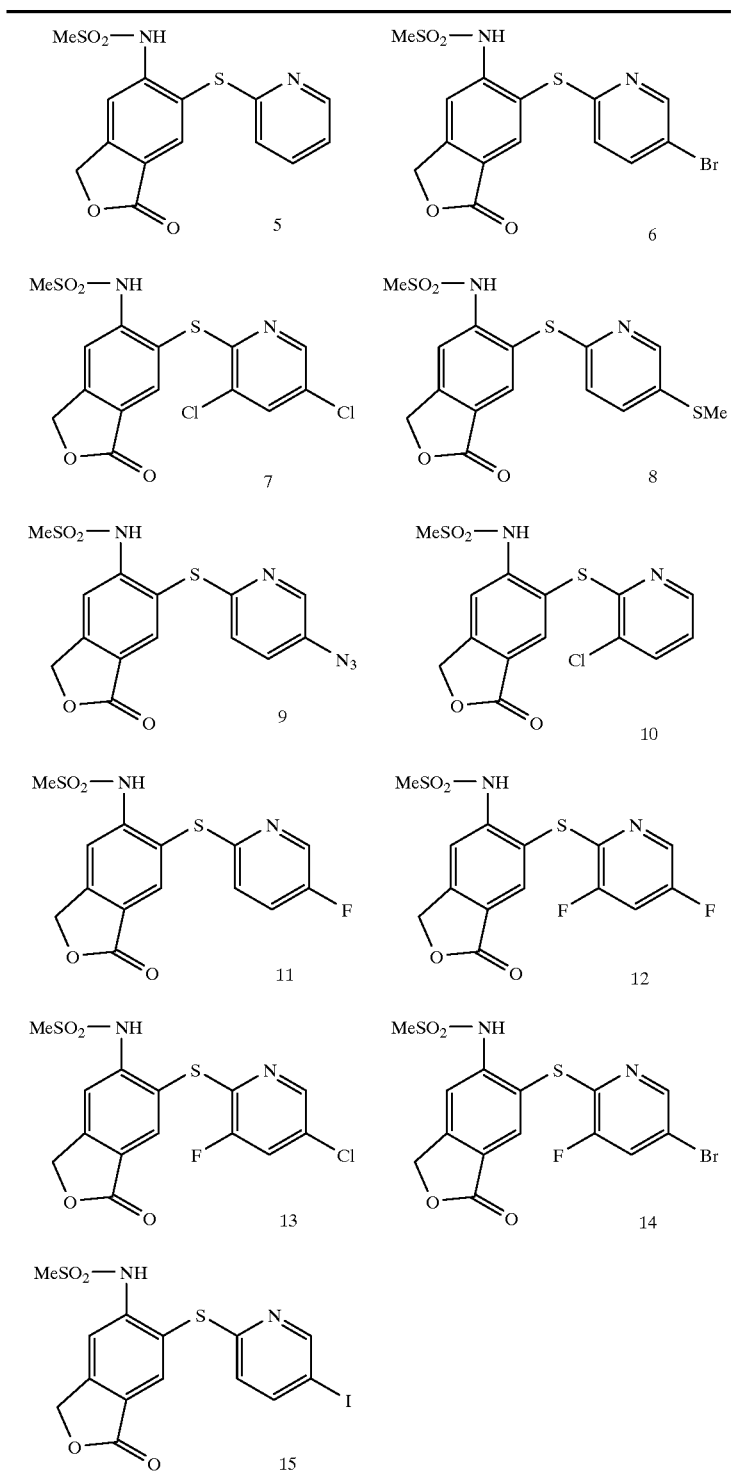

The compounds of Formula I can be tested using the following assays to determine their cyclooxygenase-2 inhibiting activity.

Inhibition of Cyclooxygenase Activity

Compounds are tested as inhibitors of cyclooxygenase activity in whole cell cyclooxygenase assays. Both of these assays measure prostaglandin $E_2$ synthesis in response to arachidonic acid, using a radioimmunoassay. Cells used for these assays are human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate.

Rat Paw Edema Assay—Protocol

Male Sprague-Dawley rats (150–200 g) are fasted overnight and are given po either vehicle (1% methocell or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 μl of 1% carrageenan solution in saline (FMC Corp, Maine) into the paw using an insulin syringe with a 25-gauge needle (i.e., 500 μg carrageenan per paw). Three h later, the paw volume ($V_3$) is measured and the increases in paw volume ($V_3-V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-Induced Gastrophathy in Rats

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of Hanks' balanced salt solution (HBSS). The red blood cells are incubated with 400 μCi of sodium $^{51}$chromate for 30 min. at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 μCi) is injected per rat.

Protein-Losing Gastropathy in Squirrel Monkeys

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 μCi/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h, and 8 h, after the last drug dose, and plasma concentrations of drug measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin E2 ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for inhibition of $PGE_2$ production may be seen in Table 2.

TABLE 2

| Example | Osteosarcoma cells (COX-2) $IC_{50}$ | U-937 Cells (COX-1) $IC_{50}$ | Rat Paw edema $ED_{30}$ |
|---|---|---|---|
| 1 | 6 nM | >100 μM | 0.16 mg/kg |
| 2 | 33 nM | >100 μM | 1.30 mg/kg |
| 3 | 140 nM | >100 μM | not done |
| 4 | 36.7 nM | >100 μM | 1.0 mg/kg |

The following abbreviations have the indicated meanings:

| | | |
|---|---|---|
| Ac | = | acetyl |
| DMAP | = | 4-(dimethylamino)pyridine |
| DMF | = | N,N-dimethylformamide |
| DMSO | = | dimethyl sulfoxide |
| EtOAc | = | Ethyl acetate |
| $Et_3N$ | = | triethylamine |
| HCl | = | Hydrochloric acid |
| Ms | = | methanesulfonyl=mesyl=$MeSO_2$- |
| NBS | = | N-bromosuccinimide |
| NSAID | = | non-steroidal anti-inflammatory drug |
| PCC | = | pyridinium chlorochromate |
| PDC | = | pyridinium dichromate |
| Ph | = | phenyl |
| r.t. | = | room temperature |
| THF | = | tetrahydrofuran |
| TLC | = | thin layer chromatography |
| Ts | = | p-toluenesulfonyl=tosyl |
| TsO | = | p-toluenesulfonate=tosylate |
| Alkyl group abbreviations | | |
| Me | = | methyl |
| Et | = | ethyl |

Statement to Precede Examples

The invention will now be illustrated by the following non-limiting examples in which, unless stated otherwise:

all operations were carried out at room or ambient temperature, that is, at a temperature in the range 18–25° C.; evaporation of solvent was carried out using a rotary evaporator under reduced pressure (600–4000 pascals: 4.5–30 mm Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

EXAMPLE 1

Preparation Examples for Method A
6-(4-Ethyl-2-thiazolythio)-5-methanesulfonamido-3H-isobenzofuran-1-one
Step 1: 5-Chloro-4-nitro-2-methylbenzonitrile To a suspension of 5-chloro-4-nitro-2-methylaniline (40.0 g, 0.21 mol) in acetone (140 mL) and $H_2O$ (150 mL) at 0° C. was added concentrated aqueous HCl (45 mL). The mixture was well stirred and a solution of $NaNO_2$ (18.0 g, 0.26 mol) in $H_2O$ (60 mL) was added dropwise over a period of 15 min. The mixture was further stirred for 20 min. and then added portionwise to a vigorously stirred mixture of CuCN (30.0 g, 0.34 mol) and NaCN (44.0 g, 0.90 mol) in $H_2O$ (200 mL):EtOAc (100 mL). After stirring at room temperature for 30 min., the mixture was diluted with $H_2O$ and extracted with EtOAc. The EtOAc extract was washed successively with 1N NaOH and brine, dried over anhydrous $MgSO_4$ and concentrated. The residue was suspended in hexanes:$Et_2O$ (1:1), stirred for 15 min., and filtered to provide the title compound (32 g, 76%) as yellow solid.

$^1$H NMR (Acetone-$d_6$): δ 8.16 (s, 1H), 8.10 (s, 1H), 2.65 (s, 3H).
Step 2: 2-Acetoxymethyl-5-chloro-4-nitrobenzonitrile A mixture of 5-chloro-4-nitro-2-methylbenzonitrile (32.0 g, 0.16 mol), NBS (54.0 g, 0.30 mol) and benzoyl peroxide (200 mg, catalytic amount) in chlorobenzene was heated at 130° C. and irradiated with a sunlamp for 15 h. More NBS (30.0 g, 0.17 mol) and benzoyl peroxide (200 mg) were added. The mixture was further reacted for 24 h. After cooling, the precipitate formed was filtered off and washed with $CH_2Cl_2$. The combined filtrates were washed with $H_2O$ (2×), dried over anhydrous $MgSO_4$ and concentrated in vacuo. The residue was then chromatographed over silica gel and eluted with hexanes:EtOAc (9:1) to give 2-bromomethyl-5-chloro-4-nitrobenzonitrile (48 g, contaminated with starting material and dibrominated product) as a pale yellow solid.

The above partially purified bromide was dissolved in DMF (300 mL) and cooled to 0° C. Sodium acetate (18.0 g, 0.22 mol) was added. The mixture was stirred at 60° C. for 30 min. After cooling, the mixture was diluted with $H_2O$ and extracted with EtOAc. The EtOAc extract was washed with $H_2O$ (2×), dried over anhydrous $MgSO_4$ and concentrated in vacuo. Chromatography over silica gel and elution with hexanes:EtOAc (9:1) yielded a front fraction containing 5-chloro-4-nitro-2-methylbenzonitrile and dibromide. Further elution with hexanes:EtOAc (2:1) gave the title compound (19.5 g, 47%) as a pale yellow solid.

$^1$H NMR (CDCl$_3$): δ 7.98 (s, 1H), 7.88 (s, 1H), 5.28 (s, 2H), 2.18 (s, 3H).
Step 3: 6-Chloro-5-nitro-3H-isobenzofuran-1-one To a solution of 2-acetoxymethyl-5-chloro-4-nitrobenzonitrile (19.5 g, 77 mmol) in MeOH:THF (600 mL, 2:1) was added a solution of 1M aqueous NaOH (100 mL, 100 mmol). After stirring at room temperature for 30 min. TLC showed no starting material remaining. The mixture was acidified with 6M aqueous HCl (100 mL, 0.6 mol), heated at 60° C. for 1 h, cooled to room temperature and stirred for 6 h. Volatile solvents were evaporated in vacuo. The residue was suspended in $H_2O$ and filtered. The solid collected was washed with $H_2O$ and dried under vacuum to give the title compound (14.5 g, 88%) as an orange-yellow solid. $^1$H NMR (CDCl$_3$): δ 8.11 (s, 1H), 7.92 (s, 1H), 5.40 (s, 2H).
Step 4: 6-Chloro-1-hydroxy-5-nitro-1,3-dihydrobenzofuran To a suspension of 6-chloro-5-nitro-3H-isobenzofuran-1-one (14.5 g, 68 mmol) in toluene at −78° C. was added neat Dibal (15 mL, 84 mmol). The mixture was stirred at −78° C. for 1 h, quenched with MeOH (20 mL) followed by 0.5M aqueous HCl (600 mL). The whole mixture was extracted with EtOAc (2×). The EtOAc extracts were combined, washed successively with dilute aqueous HCl and brine, dried over anhydrous $MgSO_4$ and concentrated in vacuo to yield the title compound (14.5 g, quantitative) as a light brown solid.

$^1$H NMR (CDCl$_3$): δ 7.78 (s, 1H), 7.62 (s, 1H), 6.52 (s, 1H), 5.15 (ABq, 2H), 3.15 (brs, 1H).
Step 5: 6-Chloro-1-methoxy-5-nitro-1,3-dihydrobenzofuran A mixture of 6-chloro-1-hydroxy-5-nitro-1,3-dihydrobenzofuran (14.5 g, 67 mmol), trimethyl orthoformate (50 mL) and p-TsOH (600 mg) in MeOH (500 mL) was stirred at room temperature for 3 h and stood at −20° C. for 12 h. The precipitate formed was collected, washed with cold MeOH and dried under vacuum to give the title compound (10.9 g, contaminated about 3–5% of starting lactol) as a light brown solid. The filtrate was treated with saturated aqueous $NaHCO_3$ and concentrated in vacuo. The residue was diluted with $H_2O$, extracted with EtOAc. The EtOAc extract was washed with $H_2O$, dried over anhydrous $MgSO_4$ and concentrated in vacuo. Chromatography over silica gel and elution with hexanes:EtOAc (4:1) yielded 1.6 g of the title compound as a pale yellow solid. Combined yield of the title compound was 12.5 g (90%).

$^1$H NMR (CDCl$_3$): δ 7.75 (s, 1H), 7.56 (s, 1H), 6.12 (s, 1H), 5.10 (ABq, 2H), 3.48 (s, 3H).
Step 6: 6-(4-Ethyl-2-thiazolythio)-1-methoxy-5-nitro-1,3-dihydrobenzofuran To a solution of 2-mercapto-4-ethylthiazole (800 mg, 5.54 mmol) (J. Org. Chem., 1941, 6, 764) in DMF (9 mL) was added powdered KOH (415 mg, 5.9 mmol). This mixture was stirred until all the base was dissolved and 6-chloro-1-methoxy-5-nitro-1,3-dihydrobenzofuran (850 mg, 3.7 mmol) was added, and the dark solution was heated to 110° C. for 3 h. After cooling to room temperature, the mixture was partitioned between $H_2O$ and EtOAc. The organic layer was washed three times with $H_2O$, one time with brine and dried over $MgSO_4$. Evaporation of the solvent and purification over silica gel using 3:3:0.5 ($CH_2Cl_2$:hexanes:EtOAc) gave the title compound (1.1 g, 88% yield) as a yellow solid.

$^1$H NMR (CDCl$_3$): δ 8.1 (s, 1H), 7.18 (s, 1H), 7.14 (s, 1H), 6.02 (s, 1H), 5.17 (d, 1H), 5.05 (d, 1H), 3.35 (s, 3H), 2.88 (q, 2H), 1.33 (t, 3H).

Step 7: 6-(4-Ethyl-2-thiazolythio)-1-hydroxy-5-nitro-1,3-dihydrobenzofuran

To a solution of 6-(4-ethyl-2-thiazolythio)-1-methoxy-5-nitro-1,3-dihydrobenzofuran (1.1 g, 3.25 mmol) in a mixture of THF:acetone (1:1) (40 mL) was added 1M hydrochloric acid (15 mL). The solution was heated at 65° C. for 2 h. After cooling the solvent was evaporated in vacuo and the oil obtained was partitioned between $H_2O$ and EtOAc. The organic layer was separated, washed with brine and dried over $MgSO_4$. Evaporation of solvent gave the title compound as a foam which was used without further purification (1.12 g).

$^1$H NMR ($CDCl_3$): δ 8.1 (s, 1H), 7.17 (s, 1H), 7.15 (s, 1H), 6.32 (s, 1H), 5.25 (d, 1H), 5.03 (d, 1H), 2.88 (q, 2H), 1.32 (t, 3H).

Step 8: 6-(4-Ethyl-2-thiazolythio)-5-nitro-3H-isobenzofuran-1-one

A mixture of 6-(4-ethyl-2-thiazolythio)-1-hydroxy-5-nitro-1,3-dihydrobenzofuran (3.25 mmol, 1.12 g), grounded molecular sieves (about 500 mg), and pyridinium dichromate (3.7 g, 10 mmol) in $CH_2Cl_2$ (30 mL) was stirred at room temperature for 2 h. $Et_2O$ (60 mL) was then added and the suspension was filtered on celite. Solvent was evaporated and the product was purified over silica gel using 3:3:1 $CH_2Cl_2$:hexane:EtOAc. The title compound was obtained as a yellow solid (750 mg, 72% for 2 steps). $^1$H NMR ($CDCl_3$): δ 8.32 (s, 1H), 7.68 (s, 1H), 7.20 (s, 1H), 5.36 (s, 2H), 2.90 (q, 2H), 1.32 (t, 3H).

Step 9: 5-Amino-6-(4-ethyl-2-thiazolylthio)-3H-isobenzofuran-1-one

A mixture of 6-(4-ethyl-2-thiazolylthio)-5-nitro-3H-isobenzofuran-1-one (750 mg, 2.33 mmol), Fe powder (600 mg, 10.7 mmol) and $NH_4Cl$ (150 mg, 2.8 mmol) in 45 mL of $EtOH:H_2O$ (2:1) was refluxed for 1.5 h. The hot mixture was filtered through celite and the celite was washed several times with hot EtOH:THF (4:1). Solvent was evaporated in vacuo and the residue was partitioned between $H_2O$ and EtOAc. The organic layer was separated, washed with brine, dried over $MgSO_4$ and concentrated. The solid title compound so obtained was used without purification in the next step.

$^1$H NMR ($CDCl_3$): δ 8.10 (s, 1H), 6.75 (s, 1H), 6.72 (s, 1H), 5.18 (s, 2H), 5.11 (brs, 2H), 2.75 (q, 2H), 1.25 (t, 3H).

Step 10: 5-Bis(methanesulfonyl)amino-6-(4-ethyl-2-thiazolythio)-3H-isobenzofuran-1-one To a solution of 5-amino-6-(4-ethyl-2-thiazolythio)-3H-isobenzofuran-1-one (10.0 g, 34.2 mmol) and $Et_3N$ (155 mmol, 21.5 mL) in $CH_2Cl_2$ (300 mL) maintained at 0° C. was added MsCl (150 mmol, 11.8 mL). This solution was stirred 1 h at 0° C. and washed with an aqueous solution of $NaHCO_3$. The organic layer was separated, washed with $H_2O$, brine and dried over $MgSO_4$. The product obtained after evaporation of solvent was purified over silica gel using hexane:EtOAc (1:2) to give the title compound as a solid 12.3 g (79% for 2 steps).

$^1$H NMR ($CDCl_3$): δ 8.03 (s, 1H), 7.52 (s, 1H), 7.00 (s, 1H), 5.35 (s, 2H), 3.55 (s, 6H), 2.80 (q, 2H), 1.28 (t, 3H).

Step 11: 6-(4-Ethyl-2-thiazolythio)-5-methanesulfonamido-3H-isobenzofuran-1-one

To a solution of 5-bis(methanesulfonyl)amino-6-(4-ethyyl-2-thiazolythio)-3H-isobenzofuran-1-one (12.3 g, 29 mmol) in MeOH:THF (3:1) (650 mL) was added at 0° C. 1M aqueous NaOH (100 mL, 100 mmol). After stirring 10 min. at 0° C., HOAc (15 mL) was added and most of the solvents were evaporated in vacuo. The residue was extracted twice using EtOAc, which was washed with $H_2O$ and brine. The organic layers were dried over $MgSO_4$ and concentrated. The residue was suspended in EtOH and filtered to give 6.0 g of the title compound. The filtrate was concentrated and purified over silica gel using hexane:ethyl acetate (1:2) to give 1.0 g more of the title compound. Combined yield was 7.0 g (65%).

$^1$H NMR ($CDCl_3$): δ 9.75 (s, 1H), 8.23 (s, 1H), 7.89 (s, 1H), 6.89 (s, 1H), 5.30 (s, 2H), 3.07 (s, 3H), 2.75 (q, 2H), 1.28 (t, 3H).

EXAMPLE 2

6-(5-Chloro-2-pyridylthio)-5-methanesulfonaido-3H-isobenzofuran-1-one

Step 1: 6-(5-Chloro-2-pyridylthio)-1-methoxy-5-nitro-1,3-dihydrobenzofuran

The title compound was prepared in the same manner as in Step 6 in Example 1, but using 5-chloro-2-mercaptopyridine.

$^1$H NMR ($CDCl_3$): δ 8.45 (s, 1H), 7.97 (s, 1H), 7.62 (d, 1H), 7.41 (s, 1H), 7.38 (d, 1H), 6.07 (s, 1H), 5.21 (d, 1H), 5.07 (d, 1H), 3.42 (s, 3H).

Step 2: 6-(5-Chloro-2-pyridylthio)-1-hydroxy-5-nitro-1,3-dihydrobenzofuran

The title compound was prepared in the same manner as Step 7 in Example 1.

$^1$H NMR ($CDCl_3$): δ 8.48 (s, 1H), 8.0 (s, 1H), 7.65 (d, 1H), 7.43 (s, 1H), 7.39 (d, 1H), 6.42 (d, 1H), 5.27 (d, 1H), 5.08 (d, 1H), 2.97 (d, 1H).

Step 3: 6-(5-Chloro-2-pyridylthio)-5-nitro-3H-isobenzofuran-1-one

The title compound was prepared in the same manner at Step 8 in Example 1.

$^1$H NMR ($CDCl_3$): δ 8.47 (s, 1H), 8.18 (s, 1H), 7.91 (s, 1H), 7.68 (d, 1H), 7.47 (d, 1H), 5.38 (s, 2H).

Step 4: 5-Amino-6-(5-chloro-2-pyridylthio)-3H-isobenzofuran-1-one

The title compound was prepared in the same manner at Step 9 in Example 1.

$^1$H NMR ($CDCl_3$+DMSO): δ 7.78 (s, 1H), 7.32 (s, 1H), 6.95 (d, 1H), 6.35 (s, 1H), 6.25 (d, 1H), 4.65 (s, 2H).

Step 5: 5-Bis(methanesulfonyl)amino-6-(5-chloro-2-pyridylthio)-3H-isobenzofuran-1-one The title compound was prepared in the same manner as Step 10 in Example 1.

$^1$H NMR ($CDCl_3$): δ 8.38 (s, 1H), 8.07 (s, 1H), 7.58 (m, 2H), 7.28 (d, 1H), 5.38 (s, 2H), 3.48 (s, 6H).

Step 6: 6-(5-Chloro-2-pyridylthio)-5-methanesulfonamido-3H-isobenzofuran-1-one

The title compound was prepared in the same manner as Step 11 in Example 1.

$^1$H NMR ($CDCl_3$): δ 8.55 (s, 1H), 8.30 (s, 1H), 8.19 (s, 1H), 7.89 (s, 1H), 7.60 (d, 1H), 7.22 (d, 1H), 5.32 (s, 2H), 3.05 (s, 3H).

EXAMPLE 3

6-(2-Thiazolythio)-5-methanesulfonamido-3H-isobenzofuran-1-one

The title compound was prepared in the same manner as Steps 6–11 in Example 1 from 6-chloro-1-methoxy-5-nitro-1,3-dihydrobenzofuran and 2-mercaptothiazole.

$^1$H NMR($CDCl_3$): δ 9.08 (brs, 1H), 8.20 (S,1H), 8.00 (S,1H), 7.80 (d,1H), 7.68 (d,1H), 5.46 (S, 2H), 3.20 (S,3H).

EXAMPLE 4

Preparation Example for Method B
5-Methanesulfonamido-6-(4-methyl-2-thiazolythio)-3H-isobenzofuran-1-one Step 1: 4-(4-Methyl-2-thiazolythio)-3-nitrobenzaldehyde To 2-mercapto-4-methylthiazole (1.81 g, 13.8 mmol) (*J. Org. Chem.*, 1941, 6, 764) in DMF (10 mL) was added powdered KOH (770 mg, 13.8 mmol). The mixture was heated at 100° C. until a homogenous solution resulted (~30 min). The mixture was cooled to room temperature and more DMF (30 mL) was added, followed by a solution of 4-chloro-3-nitrobenzaldehyde (2.56 g, 13.8 mmol) (Aldrich chemical) in DMF. The mixture was heated at 100° C. for 1 h, cooled to room temperature, diluted with $H_2O$ (200 mL) and extracted with EtOAc. The ethyl acetate extract was washed successively with 1N aqueous KOH, brine, dried over anhydrous $MgSO_4$ and concentrated in vacuo. Chromatography over silica gel and elution with hexanes:EtOAc provided the title compound as a pale yellow solid (3.4 g, 88%).

$^1$H NMR (CDCl$_3$): δ 9.99 (s, 1H), 8.68 (s, 1H), 7.90 (d, 1H), 7.26 (s, 1H), 7.18 (d, 1H), 2.58 (s, 3H).

Step 2: 4-Hydroxymethyl-1-(4-methyl-2-thiazolythio)-2-nitrobenzene

To a suspension of 4-(4-methyl-2-thiazolythio)-3-nitrobenzaldehyde (3.2 g, 11.4 mmol) in MeOH (50 mL) at 0° C. was added portionwise solid $NaBH_4$. The mixture was stirred at 0° C. for 1 h, quenched with HOAc (1 mL). Solvent was evaporated in vacuo. The residue was diluted with $H_2O$ and extracted with EtOAc. The extract was washed successively with 1N aqueous KOH and brine, dried over anhydrous $MgSO_4$ and concentrated to give the title compound (3.2 g, quantitative) as a yellow solid.

$^1$H NMR (CDCl$_3$): δ 8.20 (s, 1H), 7.42 (d, 1H), 7.16 (s, 1H), 7.02 (d, 1H), 4.76 (s, 2H), 2.55 (s, 3H).

Step 3: 4-Acetoxymethyl-1-(4-methyl-2-thiazolythio)-2-nitrobenzene

A mixture of 4-hydroxymethyl-1-(4-methyl-2-thiazolythio)-2-nitrobenzene (3.2 g, 11.3 mmol), Ac$_2$O (2.2 g, 21.6 mmol), Et$_3$N (3.63 g, 36 mmol) and DMAP (100 mg, 0.82 mmol) in CH$_2$Cl$_2$ (50 mL) was stirred at room temperature for 1 h. The mixture was then washed successively with 1N aqueous NaOH (1×), 1N aqueous HCl and brine, dried with anhydrous $MgSO_4$ and concentrated in vacuo to yield the title compound (3.6 g, quantitative).

$^1$H NMR (CDCl$_3$): δ 8.20 (s, 1H), 7.42 (d, 1H), 7.15 (s, 1H), 7.06 (d, 1H), 5.08 (s, 2H), 2.54 (s, 3H), 2.08 (s, 3H).

Step 4: 4-Acetoxymethyl-2-amino-1-(4-methyl-2-thiazolythio)benzene

A mixture of 4-acetoxymethyl-1-(4-methyl-2-thiazolythio)-2-nitrobenzene (3.6 g, 11.1 mmol), Fe powder (5.0 g, 89 mmol) and NH$_4$Cl (500 mg, 9.3 mmol) in 150 mL of EtOH:H$_2$O (2:1) was refluxed for 1 h. The hot mixture was filtered through celite. The solvent was evaporated in vacuo. The residue was diluted with $H_2O$ and extracted with EtOAc. The EtOAc extract was washed with brine, dried over anhydrous $MgSO_4$ and concentrated to give the title compound (3.2 g, quantitative).

$^1$H NMR (CDCl$_3$): δ 7.50 (d, 1H), 6.78 (s, 1H), 6.72 (d, 1H), 6.68 (s, 1H), 5.02 (s, 2H), 2.38 (s, 3H), 2.02 (s, 3H).

Step 5: 4-Acetoxymethyl-2-methanesulfonamido-1-(4-methyl-2-thiazolythio)benzene

A mixture of 4-acetoxymethyl-2-amino-1-(4-methyl-2-thiazolythio)benzene (3.2 g, 10.9 mmol), pyridine (3.0 g, 38 mmol) and MsCl (1.5 mL, 19.5 mmol) in CH$_2$Cl$_2$ (50 mL) was stirred at room temperature for 24 h. The mixture was then washed with 1N aqueous HCl and brine, dried over anhydrous $MgSO_4$ and concentrated in vacuo. Chromatography over silica gel and elution with hexanes: EtOAc (1:1) yielded the title compound (3.0 g, 75%) as a solid.

$^1$H NMR (CDCl$_3$): δ 8.95 (brs, 1H), 7.74 (s, 1H), 7.66 (d, 1H), 7.14 (d, 1H), 6.80 (s, 1H), 5.10 (s, 2H), 3.00 (s, 3H), 2.40 (s, 3H), 2.12 (s, 3H).

Step 6: 4-Acetoxymethyl-2-methanesulfonamido-1-(4-methyl-2-thiazolythio)-5-nitrobenzene To a solution of 4-acetoxymethyl-2-methanesulfonamido-1-(4-methyl-2-thiazolythio)benzene (3.0 g, 8.1 mmol) in TFA (35 mL) at room temperature was added a solution of 2.5M aqueous NaNO$_3$ (3.5 mL, 8.8 mmol). The mixture was heated at 70° C. for 1 h. Nitrogen dioxide gas evolved at some point. Solvent was removed in vacuo. The residue was diluted with $H_2O$. The precipitate formed was collected, washed with $H_2O$ and dried under vacuum. The dried crude product was then suspended in EtOH, stirred for 15 min. and filtered to give the title compound (2.7 g, 80%) as a pale yellow solid.

$^1$H NMR (CDCl$_3$): δ 9.62 (brs, 1H), 8.51 (s, 1H), 7.99 (s, 1H), 6.92 (s, 1H), 5.56 (s, 2H), 3.06 (s, 3H), 2.42 (s, 3H), 2.20 (s, 3H).

Step 7: 4-Acetoxymethyl-5-amino-2-methanesulfonamido-1-(4-methyl-2-thiazolythio)benzene A mixture of 4-acetoxymethyl-2-methanesulfonamido-1-(4-methyl-2-thiazolythio)-5-nitrobenzene (1.2 g, 2.88 mmol) and 10% palladium on charcol in EtOAc (30 mL) was hydrogenated under 50 psi at room temperature for 16 h. The catalyst was filtered off through celite. Solvent was evaporated in vacuo to yield the title compound (1.1 g, quantitative) as an oily residue.

$^1$H NMR (CDCl$_3$): δ 8.70 (brs, 1H), 7.56 (s, 1H), 7.02 (s, 1H), 6.84 (s, 1H), 5.04 (s, 2H), 2.98 (s, 3H), 2.40 (s, 3H), 2.08 (s, 3H).

Step 8: 6-Acetoxymethyl-1-iodo-4-methanesulfonamido-3-(4-methyl-2-thiazolythio)benzene To a solution of 4-acetoxymethyl-5-amino-2-methanesulfonamido-1-(4-methyl-2-thiazolythio)benzene (1.0 g, 2.58 mmol) in acetone (5 mL) at 0° C. was added 6M aqueous HCl (1 mL), followed by a solution of 4M aqueous NaNO$_2$ (800 mL, 3.2 mmol). The mixture was stirred for ~15 min. A solution of 2.5M aqueous NaI (5 mL, 12.5 mmol) was then added. The mixture was slowly warmed to room temperature and stirred for ~30 min. After dilution with $H_2O$, the mixture was extracted with EtOAc. The EtOAc extract was washed with aqueous Na$_2$S$_2$O$_3$, brine, dried over anhydrous $MgSO_4$ and concentrated. Chromatography over silica gel and elution with hexanes:EtOAc (1:1) yielded the title compound (700 mg, 54%) as a white solid.

$^1$H NMR (CDCl$_3$): δ 9.15 (brs, 1H), 8.12 (s, 1H), 7.75 (s, 1H), 6.86 (s, 1H), 5.05 (s, 2H), 3.00 (s, 3H), 2.40 (s, 3H), 2.18 (s, 3H).

Step 9: 6-Hydroxymethyl-1-iodo-4-methanesulfonamido-3-(4-methyl-2-thiazolythio)benzene A mixture of 6-acetoxymethyl-1-iodo-4-methanesulfonamido-3-(4-methyl-2-thiazolythio)benzene (700 mg, 1.41 mmol) and 1M aqueous NaOH in 60 mL of MeOH:THF (2:1) was stirred at room temperature for 30 min. and then quenched with HOAc (500 µL). Solvent was removed in vacuo. The residue was diluted with $H_2O$, extracted with EtOAc. The EtOAc extract was washed with $H_2O$ (2×), dried over anhydrous $MgSO_4$ and concentrated to yield the title compound (640 mg, quantitative) as a white solid.

$^1$H NMR (CDCl$_3$): δ 9.00 (brs, 1H), 8.10 (s, 1H), 7.88 (s, 1H), 6.85 (s, 1H), 4.65 (s, 2H), 3.02 (s, 3H), 2.40 (s, 3H).

Step 10: 5-Methanesulfonamido-6-(4-methyl-2-thiazolythio)-3H-isobenzofuran-1-one A mixture of 6-hydroxymethyl-1-iodo4-methanesulfonamido-3-(4-methyl-2-thiazolythio)benzene (640 mg, 1.4 mmol), $K_2CO_3$ (380 mg, 2.8 mmol) and bis(triphenylphosphine)palladium (II) chloride (30 mg, 0.04 mmol) in DMF (10 mL) was heated under a carbon monoxide atmosphere (balloon) at 110° C. for 48 h. After cooling, the mixture was diluted with $H_2O$, acidified with HOAc and extracted with EtOAc. Some insoluble material was removed by filtration through celite. The EtOAc layer was separated, washed with $H_2O$, dried over anhydrous $MgSO_4$ and concentrated. Chromatography over silica gel and elution with hexanes:EtOAc gave the title compound (220 mg, 44%) as a white solid.

$^1$H NMR ($CDCl_3$): δ 9.48 (brs, 1H), 8.24 (s, 1H), 7.88 (s, 1H), 6.88 (s, 1H), 5.30 (s, 2H), 3.08 (s, 3H), 2.40 (s, 3H).

What is claimed is:

1. A compound of formula I

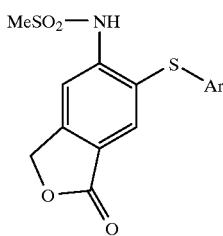

I or a pharmaceutically acceptable salt thereof wherein where Ar is

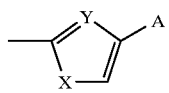

X is O or S,
Y is CH or N,
and A is selected from
  (a) hydrogen,
  (b) $C_{1-2}$ alkyl,
  (c) vinyl, and
  (d) acetylenyl;
or where Ar is

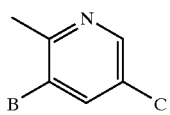

B and C are each independently
  (a) hydrogen,
  (b) F, Cl, Br or I,
  (c) methyl or ethyl,
  (d) vinyl or acetylenyl,
  (e) $OCH_3$ or $OCF_3$,
  (f) $SCH_3$, or $SCF_3$,
  (g) CN, or
  (h) $N_3$.

2. A compound according to claim 1 wherein
X is S,
Y is CH or N,
and A is selected from
  (a) hydrogen,
  (b) $C_{1-2}$alkyl,
  (c) vinyl, and
  (d) acetylenyl;
B and C are each independently
  (a) hydrogen,
  (b) F, Cl, Br or I,
  (c) methyl or ethyl,
  (d) $OCH_3$ or $OCF_3$,
  (e) $SCH_3$, or
  (f) CN.

3. A compound according to claim 2 wherein
X is S,
Y is N,
and A is selected from
  (a) hydrogen,
  (b) $C_{1-2}$ alkyl,
  (c) vinyl, and
B and C are each independently
  (a) hydrogen,
  (b) F, Cl or Br,
  (c) methyl or ethyl,
  (d) $OCH_3$,
  (e) $SCH_3$, or
  (f) CN.

4. A compound according to claim 3 wherein
X is S,
Y is N,
and A is selected from
  (a) hydrogen,
  (b) $C_{1-2}$ alkyl,
B and C are each independently
  (a) hydrogen,
  (b) F, Cl or Br,
  (c) methyl or ethyl,
  (e) $SCH_3$.

5. A compound selected from the group consisting of:
6-(4-Ethyl-2-thiazolythio)-5-methanesulfonamido-3H-isobenzofuran-1-one;
6-(5-Chloro-2-pyridylthio)-5-methanesulfonamido-3H-isobenzofuran-1-one;
6-(2-Thiazolythio)-5-methanesulfonamido-3H-isobenzofuran-1-one; and
5-Methanesulfonamido-6-(4-methyl-2-thiazolythio)-3H-isobenzofuran-1-one.

6. A pharmaceutical composition for treating an inflammatory disease susceptable to treatment with an non-steroidal anti-inflammatory agent comprising:
a non-toxic therapeutically effective amount of a compound according to claim 1 and a pharmaceutically acceptable carrier.

7. A pharmaceutical composition for treating cyclooxygenase mediated diseases advantageously treated by an active agent that selectively inhibits COX-2 in preference to COX-1 comprising:
a non-toxic therapeutically effective amount of a compound according to claim 1 and a pharmaceutically acceptable carrier.

8. A method of treating an inflammatory disease susceptible to treatment with a non-steroidal anti-inflammatory agent comprising:
administration to a patient in need of such treatment of a non-toxic therapeutically effective amount of a compound according to claim 1 and a pharmaceutically acceptable carrier.

9. A method of treating cyclooxygenase mediated diseases advantageously treated by an active agent that selectively inhibits COX-2 in preference to COX-1 comprising:

administration to a patient in need of such treatment of a non-toxic therapeutically effective amount of a compound according to claim 1.

10. A pharmaceutically acceptable salt of a compound of formula (I), as defined in claim 1.

11. An anti-inflammatory pharmaceutical composition comprising a non-toxic, therapeutically effective amount of a compound of formula (I), as defined in claim 1 or a pharmaceutically accepted carrier.

12. An anti-inflammatory pharmaceutical composition comprising a non-toxic, therapeutically effective amount of a compound of claim 5, in association with a pharmaceutically acceptable carrier.

* * * * *